Figure 1:
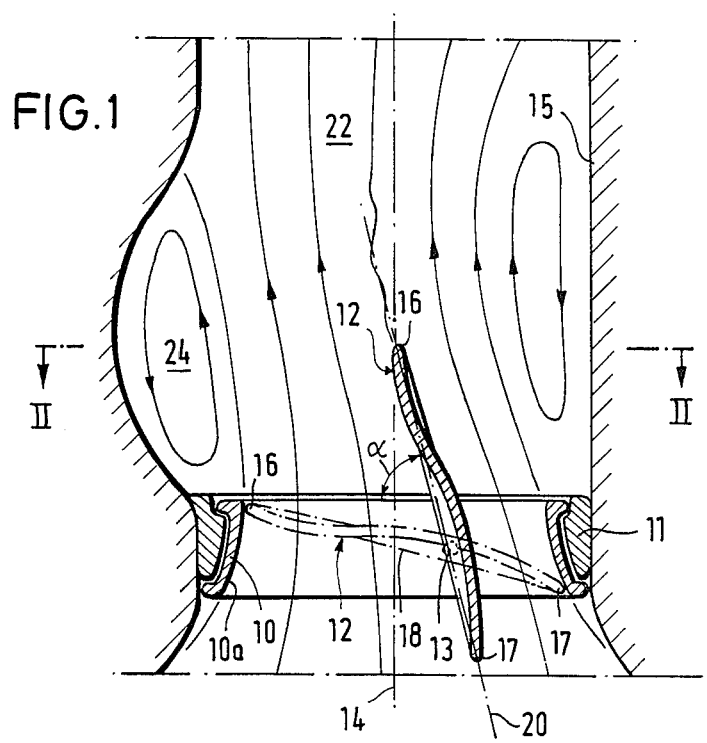

United States Patent [19]

Knoch et al.

[11] Patent Number: 4,775,378
[45] Date of Patent: Oct. 4, 1988

[54] CARDIAC VALVE PROSTHESIS

[75] Inventors: Martin Knoch, Aachen; Helmut Reul, Düren; Günter Rau, Aachen, all of Fed. Rep. of Germany

[73] Assignee: B. Braun Melsungen AG, Melsungen, Fed. Rep. of Germany

[21] Appl. No.: 145,883

[22] Filed: Jan. 20, 1988

[30] Foreign Application Priority Data

Jan. 22, 1987 [DE] Fed. Rep. of Germany ....... 3701702

[51] Int. Cl.$^4$ .............................................. A61F 2/24
[52] U.S. Cl. ...................................................... 623/2
[58] Field of Search ........................................... 623/2

[56] References Cited

U.S. PATENT DOCUMENTS 3,113,586 12/1963 Edwards ................................. 623/2
4,532,659 8/1985 Kaster .................................... 623/2

FOREIGN PATENT DOCUMENTS 2753159 5/1979 Fed. Rep. of Germany .......... 623/2

Primary Examiner—Richard J. Apley
Assistant Examiner—James Prizant
Attorney, Agent, or Firm—Spensley Horn Jubas & Lubitz

[57] ABSTRACT

A cardiac valve prosthesis having an S-shaped curve of the closing body along the skeleton line. The inlet area and the outlet area are oriented toward the flow direction, while the opening force is exclusively effective in the central region behind the swivel axis. The S-shaped geometry favors the formation of a stable, closed vortex on the suction side of the closing body with a resultant reduction of deadwater in the aorta ascendens and a more favorable closing behavior. The aortic wall is less stressed, the aorta ascendens is better washed out, and pressure loss in the area of the opening angle is relatively low.

7 Claims, 3 Drawing Sheets

CARDIAC VALVE PROSTHESIS

The invention relates to a cardiac valve prosthesis.

Natural cardiac valves are of the tricuspid or biscupid type which, technically speaking, function as nonreturn valves allowing blood to flow unidirectionally, while the counterdirection is blocked. If natural cardiac valvess are replaced by mechanical prostheses of the pendulum type or tilting disk type, monocuspid or biscupid valves are inserted wherein valvular closing bodies in a valve ring fixed by sewing to the respective heart opening are movable by blood pressure or blood flow. However, from a long-term use of such cardiac valve prostheses, serious problems which may result for a patient may entail his lifelong taking of anticoagulants or an interchange of the prosthesis.

In case of the known monocuspid cardiac valve prostheses, the closing body consists of a plane or curved valve or of a profile body which is formed like an aircraft wing. A cardiac valve prosthesis of known type (German OS No. 27 53 159) comprises a closing body curved such that its skeleton line extending transversely to the swivel axis is deflected in the main flow direction to thus achieve an increased opening angle.

It is a disadvantage common to monocuspid valvular prostheses that also in case of a complete opening position, the flow needs to be deviated unilaterally in order to generate a sufficient opening moment, said opening moment by which the closing body is pressed against its abutment resulting substantially from the changed flow direction. Hence, as a primary condition for a large opening angle, a strong flow deviation caused by the closing body is required. In case of aortic valve replacement, the resultant flow shape is unphysiological. As a consequence thereof, pressure losses are relatively high and the deadwater region in the aorta ascendens is extensive. The turbulence of the flow is strong, and also in the main flowing phase, the flow is subjected to great fluctuations, because the vortex structures emanating from the jet boundaries irregularly float away. In the upper region of the aortic sinus, there is formed unilaterally a significant stagnation point stressing the aortic wall.

It is an object of the invention to further develop a cardiac valve prosthesis in which, in opened position, the effective opening moment is sufficiently large without entailing too strong a deviation of the blood flow towards the aortic wall.

In case of the cardiac valve prosthesis of the invention, the skeleton line, i.e. the center line of the profile is S-shaped in the central plane of the closing body extending transversely to the swivel axis. By this means, the flow at the predetermined opening angle extends in parallel to the leading edge of the closing body, while the flow is deviated within the range of the closing body center or downstream of the eccentrically arranged swivel axis, so that the opening moment is exclusively generated in the central range of the closing body. The trailing edge is also directed in parallel to the main flowing direction. Due to the S-shaped geometry, the formation of a stable, closed vortex on the suction side of the closing body is favored with a resultant reduction of the deadwater area in the aorta ascendens. The flow being lesser deviated than in case of a convex-concave closing body geometry and being subsequently conducted again in parallel to the aortic axis, the swivel movement for opening and closing may be decisively reduced for a comparable pressure loss. While, normally, the opening angle is 80°, it is in the order of 72° in case of the cardiac valve prosthesis of the invention. Further, due to the more favorable flow path at the closing body, the impact pressure at the aortic wall is lower.

The stable vortex existing during the main flow phase is increased with the pressure reversal towards the systolic end thus substantially supporting the closing operation. The closing noise is weaker due to the damping effect of the vortex. Upon the closure of the valve, the aortic sinuses are extensively washed out during diastole and by the reduction of the deadwater area, the risk of thrombus formation is less serious thus substantially diminishing the lifelong requirement for a patient to take anticoagulants.

Due to an additional curve of the closing body in transverse direction to the skeleton line, the lateral edge flow around the closing body is favored. In opening position, the closing body is curved out of the swivel axis towards the ring axis. Thus, the vortex situated downstream of the swivel axis is intensified on the suction side and the deadwater in the aorta ascendens is washed out by two oppositely directed vortex tops expanding in flow direction. While the pressure losses in this embodiment are slightly increased by the dissipation of the secondary flow, this is compensated by the advantage of large vortex structures.

The subclaims relate to favorable further configurations of the invention.

Figure 2:
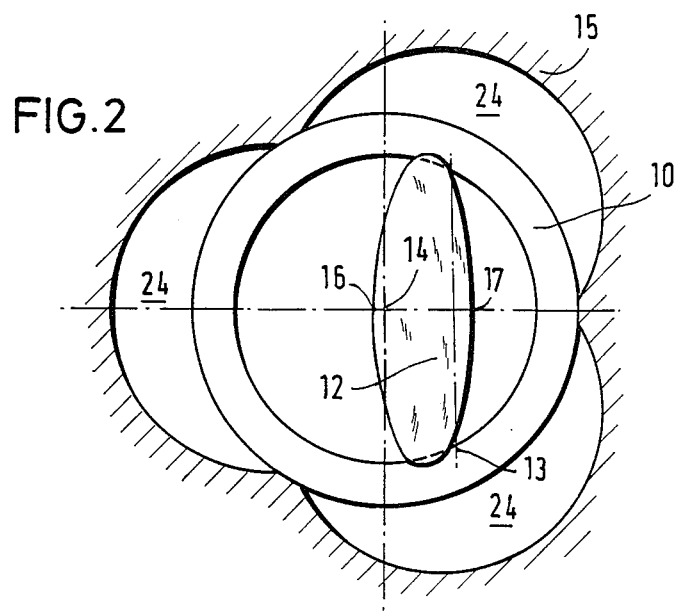
Figure 3:
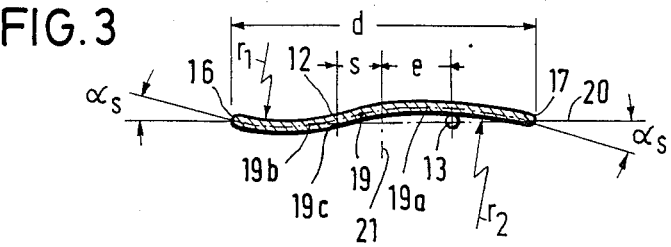
Figure 4:
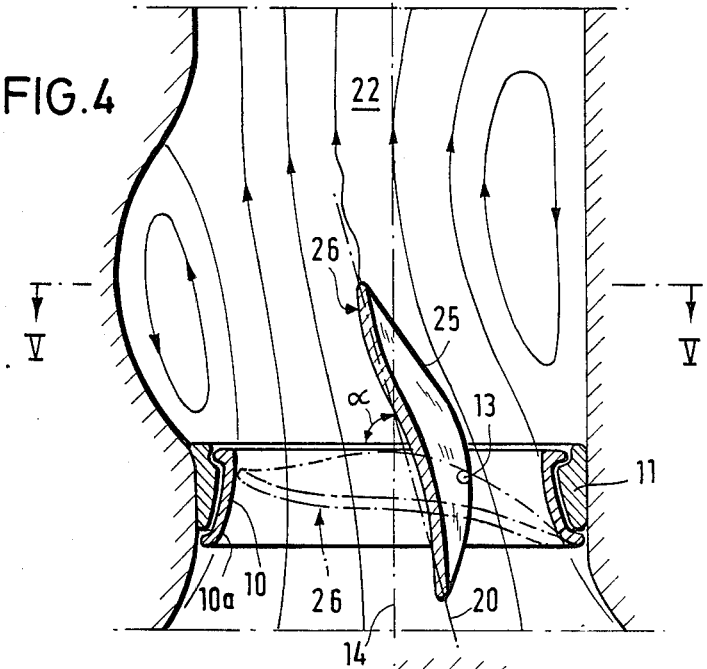
Figure 5:
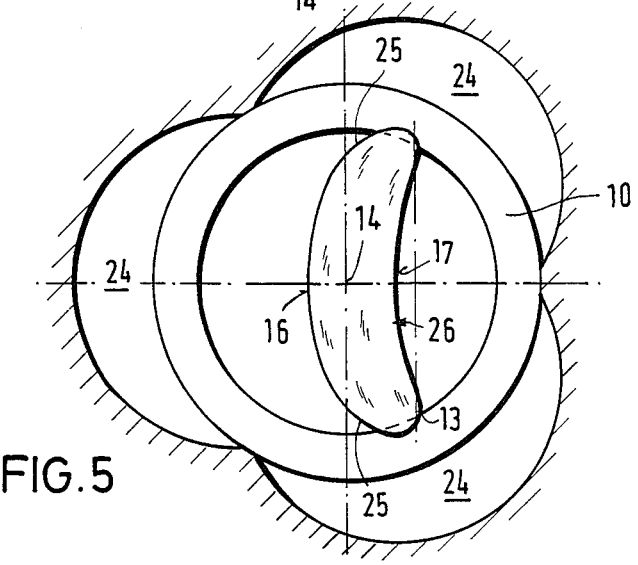
Figure 6:
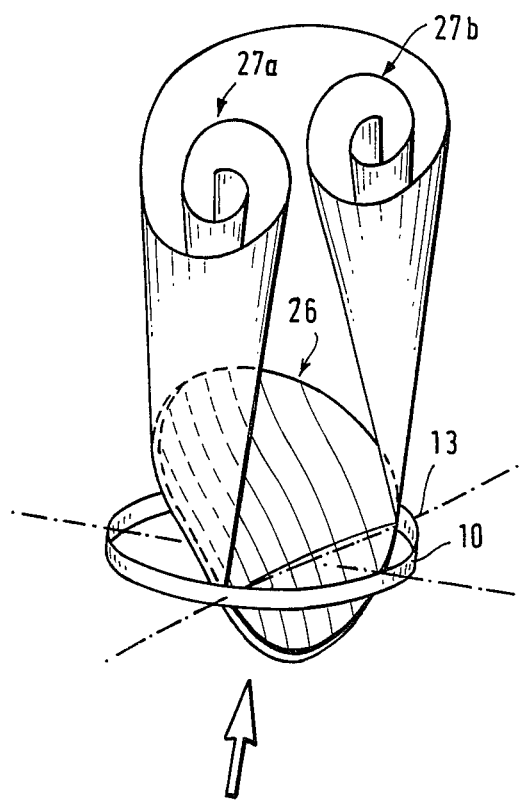

Some embodiments of the invention are explained hereunder in more detail in the drawings in which FIG. 1 is a cross section of an implanted cardiac valve prosthesis, FIG. 2 is a section along line II—II of FIG. 1, FIG. 3 is a separate view of the closing body to explain its geometry, FIG. 4 is a second embodiment of the cardiac valve prosthesis in implanted condition, FIG. 5 is a section along line V—V of FIG. 4 and FIG. 6 shows the vortex structure of the flow in case of a cardiac valve prosthesis according to FIGS. 4 and 5.

The cardiac valve prosthesis of FIGS. 1 to 3 comprises a circular valve ring 10 whose rotationally symmetric inner area 10a is continuously and increasingly constricted in flow direction, the valve ring 10 being enclosed by a sewing ring 11 which may be fixed by sewing to the aortic tissue 15. The closing body 12 is pivotally supported in the valve ring 10, the swivel axis 13 being provided eccentrically, i.e. spaced from the ring axis 14.

The closing body 12 consists of a rigid sheetmaterial of a wall thickness preferably uniform at all points. In closed position, the external edge 16 of the big wing portion rests internally against the outlet area of the inner face 10a while the external edge 17 of the smaller wing portion is applied against the inlet area of the inner face 10a. In other words, in closed position, the closing body 12 is situated diagonally inside the valve ring such as illustrated in FIG. 1. In opened position, the closing body main plane in which edges 16 and 17 are situated extends at an opening angle relative to the ring plane, the angle being 65° to 75°. Due to a (non-illustrated) abutment, the opening movement of the closing body 12 is limited with respect to the valve ring 10. The swivel axis 13 is not a physical but a geometric axis on which two bearing pins are provided which project to opposite sides from the edge of the closing body 12 and disappear in corresponding bearing recesses of the valve ring 10. The circumjacent edge 18 of the closing body located in one sole plane is shaped substantially elliptically for its adaptation to the geometry of the inner face 10a of the valve ring 10. Edges 16 and 17 form part of said edge 18.

FIG. 3 shows the course of the skeleton line of the closing body 12, the skeleton line referring to the center line of the profile which is situated in a plane extending transversely to the swivel axis 13, namely in the transverse central plane of the closing body. In said plane, the S-shape characteristic of the closing body is most developed; as the distance from the skeleton line plane (towards the swivel axis 13) increases, the S-shape grows flatter and flatter to finally end in the plane edge 18.

Portion 19a of the skeleton line adjacent to the swivel axis 13 is curved towards the main flow direction (when the closing body is closed), while portion 19b away from the swivel axis 13 is curved in counterdirection. Both portions 19a and 19b form respective circular arcs, in which the radius $r_2$ of portion 19a is longer than radius $r_1$ of portion 19b. At the turning point 19c, both portions 19a and 19b smoothly merge into one another. Through said turning point 19, there also extends the chord 20 traversing edges 16 and 17. The distance of the two edges 16 and 17 from the skeleton line, i.e. the diameter of the closing body 12 is designated with d. The distance of the swivel axis 13 from the central axis 21 of the closing body is e and the distance of the turning point 19c from the central axis 21 is s. Angle $\alpha_s$ at which the edge region 18 extends relative to chord 20 is equal to the angle at which the edge region 16 extends relative to chord 20. Said angle $\alpha_s$ is preferably 5° to 15°. A preferred range for the quotient e:d is 0.15 to 0.25, and a preferred range for quotient s:d is 0.1 to 0.2.

The radii of $r_1$ and $r_2$ of the curved portions 19b and 19a correspond to the following equations:

$$r_1 = \frac{\frac{1}{2} - \frac{1}{2}\frac{s}{d}}{\sin\alpha_s} \cdot d$$

$$r_2 = \frac{\frac{1}{2} + \frac{1}{2}\frac{s}{d}}{\sin\alpha_s} \cdot d$$

According to FIG. 1, the disclosed closing body is additionally shown in opened position, the flow lines resulting during the opened position of the closing body being indicated. As evident, the cardiac valve prosthesis is provided at the inlet of the aorta ascendens 22, in which, behind the cardiac valve, three radially arranged aortic sinuses 24 are present and surround the cusps of the natural trileaflet cardiac valve. If the latter is removed to be replaced by a prosthesis, the aortic sinuses 24 influence the blood flow, whereby recirculation areas or deadwater areas are formed. As shown in FIGS. 1 and 2, the cardiac valve prosthesis is so provided that the opened closing body 12 extends nearly in parallel to the one aortic sinus 24. As evident, in opened position, the edges 16 and 17 are aligned in parallel to the arriving or departing flow. Due to the force exerted by the flow onto the central region of the closing body 12, the latter is urged into the opened position and kept pressed against the (non-illustrated) abutment. If the opening force is sufficient for a flutter-free abutment, the flow is not substantially deviated by the opened closing body. In particular, the blood flow is not concentrated on a specific site of the aortic wall thus excluding the formation of a characteristic stagnation point. In spite of the smaller opening angle, the pressure loss caused by the closing body is lower than in case of the usual convex-concave closing bodies. The closing time and the reflux volume are considerably reduced because of the smaller swivel angle and of the larger working surface at the moment of the beginning reflux.

In case of the cardiac valve prosthesis shown in FIGS. 4 and 5, the valve ring 10 is of the same design as that of the first embodiment, and also the skeleton line of the closing body 26 corresponds to that of the closing body of the first embodiment. There is only a difference in that the closing body 26 is additionally curved transversely to the plane of the skeleton line cross section corresponding to the sectional plane of FIG. 4. Due to said curve, the cross section of the smaller opening formed in the valve ring is increased if the closing body is in opened position. Further, unfavorable acute angles between the inner ring surface and the closing body surfaces are avoided at the bearing points. As a result thereof, the aorta ascendens is better washed out and the tendency to thrombus formation is additionally lessened. Further, as another advantage of this embodiment, the opening and closing moments are increased by an increased lever arm for the attacking flow forces. In this embodiment, the lateral edges 25 do not extend in a plane, but (with a closing body 26 in the closed position) in flow direction. The swivel axis 13 to which, in the vicinity of the lateral edges, the closing body is hinge-connected with the valve ring 10, is downstream of the skeleton line of the closing body, while, pursuant to the first embodiment, it is provided upstream of the skeleton line. Also for the second embodiment, the maximum opening angle is 65° to 75°.

FIG. 6 shows the course of the edge flow around the closing body 26. The two vortices 27a and 27b are clearly visible in which the flow rotates around axes extending parallel to the ring axis and which ensure that the deadwater in the aorta ascendens is washed out. Said vortices 27a and 27b start from the swivel axis 13 to expand in flow direction.

Although the cardiac valve prosthesis disclosed above is based on its use as an aortic valve, it may be used in the same way, after a modification of the textile sewing ring 11, as a mitral valve.

What is claimed is:

1. Cardiac valve prosthesis for controlling fluid flow comprising
   a valve ring having a ring axis,
   a closing body pivotally supported about a swivel axis extending transversely to and spaced from the ring axis, the closing body being pivotable between an open position and a closed position,
   the closing body having a substantially curved, S-shaped skeleton line which extends in a plane normal to the swivel axis, the closing body further comprising
   a first portion curved in the direction of fluid flow in the closed position, and
   a second portion curved oppositely to the direction of fluid flow in the closed position,
   the first portion being spaced closer to the swivel axis than the second portion.

2. Cardiac valve prosthesis as defined in claim 1, wherein the first portion includes an external end region and the second portion includes an external end region and wherein the external end regions of the first portion and the second portion form angles of 5° to 15° with a chord intersecting the edges of the closing body along the skeleton line.

3. Cardiac valve prosthesis as defined in claim 1, further comprising a turning point situated between the first portion and the second portion and situated on the skeleton line approximately midway between the swivel axis and the end region of the second portion.

4. Cardiac valve prosthesis as defined in claim 2, further comprising a turning point situated between the first portion and the second portion and substantially on the chord.

5. Cardiac valve prosthesis as defined in claim 1, wherein the closing body includes a peripheral line and the peripheral line of the closing body extends in a single plane.

6. Cardiac valve prosthesis as defined in claim 1, wherein, transversely to the plane normal to the swivel axis, the closing body is curved away from the swivel axis and toward the ring axis in the open position, the closing body being symmetric about the skeleton line.

7. A cardiac valve prosthesis for controlling fluid flow comprising:
   a valve ring having a ring axis,
   a closing body pivotally supported about a swivel axis extending transversely to and spaced from the ring axis, the closing body be pivotable between an open position and a closed position, the closing body further comprising:
   a substantially curved, S-shaped skeleton line extending in a plane normal to the swivel axis,
   a first portion curved toward the direction of fluid flow in the closed position, and
   a second portion curved away from the direction of fluid flow in the closed position,
   the first portion being spaced closer to the swivel axis than the second portion.

* * * * *